US00PP32285P2

(12) United States Plant Patent
Van Swieten

(10) Patent No.: US PP32,285 P2
(45) Date of Patent: Oct. 6, 2020

(54) ***PHALAENOPSIS* ORCHID PLANT NAMED 'PHALGOPXO'**

(50) Latin Name: ***Phalaenopsis* hybrid**
Varietal Denomination: PHALGOPXO

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 16/873,013

(22) Filed: Jan. 15, 2020

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62
See application file for complete search history.

(56) References Cited

PUBLICATIONS

UPOV hit on *Phalaenopsis* plant named 'PHALGOPXO', QZ PBR 53013, filed Apr. 26, 2018.*

* cited by examiner

*Primary Examiner* — Anne Marie Grunberg
(74) *Attorney, Agent, or Firm* — Jondle & Associates, P.C.

(57) ABSTRACT

A new and distinct variety of *Phalaenopsis* plant named 'PHALGOPXO', particularly characterized by having light yellow-green, flecked flowers with yellowish-pink and red lips, petals with a recurving curvature of the longitudinal axis, a convex flower shape, and is propagated by meristem tissue culture, is disclosed.

3 Drawing Sheets

Genus and species: *Phalaenopsis* hybrid.
Variety denomination: 'PHALGOPXO'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALGOPXO'.

The new *Phalaenopsis* plant is a product of a planned breeding program conducted by the inventor in Bleiswijk, the Netherlands. The objective of this breeding program was to create a new *Phalaenopsis* plant with numerous attractive, medium size light yellow-green, flecked flowers with yellowish-pink and red lips, suitable for potted plant production.

The new *Phalaenopsis* plant 'PHALGOPXO' is a result of cross-pollination made by the inventor in March 2009 in Bleiswijk, the Netherlands, of the proprietary female, or seed parent, *Phalaenopsis* hybrid '21864-014' (unpatented) with the proprietary male, or pollen parent, *Phalaenopsis* hybrid '01-2083' (unpatented).

The new *Phalaenopsis* was selected by the inventor as a single plant within the progeny of the stated cross-pollination in a controlled greenhouse in Bleiswijk, the Netherlands, in March 2012. Asexual reproduction of the new *Phalaenopsis* plant by meristem tissue culture since 2014 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Apr. 26, 2018, by Applicant who obtained the subject matter disclosed directly from the inventor. 'PHALGOPXO' has not been made publicly available or sold anywhere in the world prior to the effective filing date of this application with the exception of sales or disclosures made one year or less before the effective filing date of this claimed invention by Applicant who obtained 'PHALGOPXO' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALGOPXO' as a new and distinct variety of *Phalaenopsis* plant:

1) Light yellow-green, flecked flowers with yellowish-pink and red lips;
2) Petals with a recurving curvature of the longitudinal axis; and
3) Convex flower shape.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in November 2019. Colors in the photographs may differ from the color values cited in the detailed botanical description, which accurately describe the actual colors of the new variety.

DESCRIPTION OF THE NEW VARIETY

Figure 1:
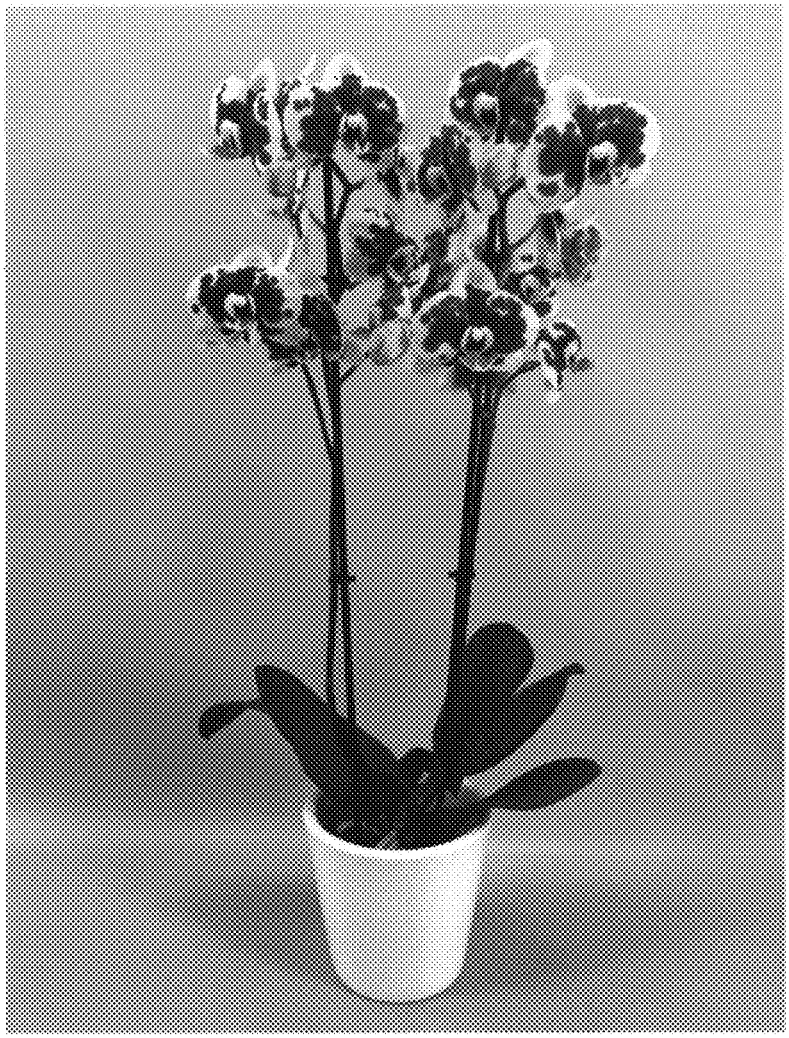
FIG. 1 shows the overall plant habit, including blooms, buds, and foliage of 'PHALGOPXO'.
Figure 2:
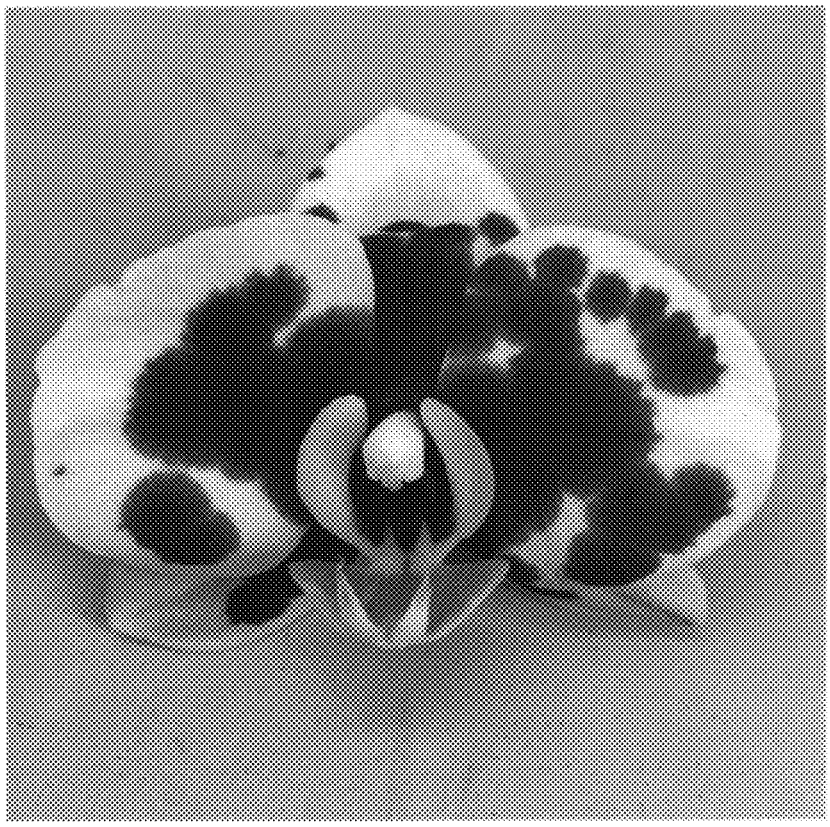
FIG. 2 shows a close-up of a flower of 'PHALGOPXO'.
Figure 3:
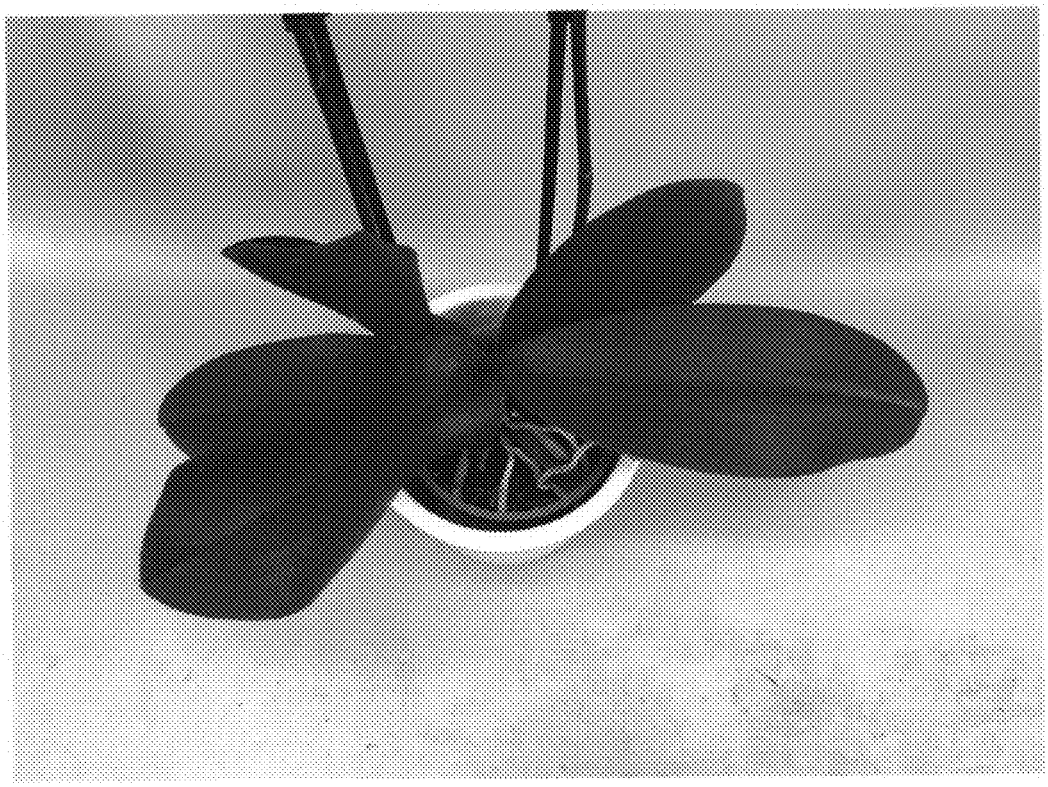
FIG. 3 shows an overhead view of the leaves of 'PHALGOPXO'.

The following detailed description sets forth the distinctive characteristics of 'PHALGOPXO'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in November 2019 on flowering plants which were planted in 12-centimeter (diameter) pots. After in-vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALGOPXO'.

Parentage:

*Female parent*.—*Phalaenopsis* cultivar '21864-014' (unpatented).

*Male parent*.—*Phalaenopsis* cultivar '01-2083' (unpatented).

Propagation:

*Type*.—Meristem tissue culture.

Roots:

*Root description*.—Greyed-green (between RHS 190B and 190C) colored roots with branching lateral roots having yellow-green (RHS 146D) colored root tips.

Plant:

*Commercial crop time to flowering*.—Following asexual propagation (in-vitro), the rooted cuttings grow for 20-24 weeks. After transplantation into 12-cm pots, the plants are finished after 48 to 50 weeks.

*Growth habit of the peduncle*.—Upright to slightly pendant with panicle inflorescence.

*Height (from soil level to top of inflorescence)*.—Approximately 55.0 cm to 60.0 cm.

*Width (measured from leaf tips)*.—About 29.0 cm to 31.0 cm.

*Vigor*.—Strong.

Leaves:

*Mature leaves*.—Quantity per plant: 6 to 8 leaves are produced before flowering. Length (fully expanded): 17.0 cm to 20.0 cm. Width: 8.0 cm to 10.0 cm. Position of the broadest part of the leaf: Toward the apex or in the middle. Shape: Oblong. Base shape: Moderately elongated. Apex: Obtuse unequal. Leaf blade angle with the petiole (measured from the horizontal position): Between 20 degrees and 40 degrees. Leaf margin: Entire. Color: Upper surface: RHS 147A. Lower surface: RHS 146A and purple (RHS N77A) toward margin and toward apex. Texture: Upper surface: Slightly rough. Lower surface: Smooth. Thickness: 2.2 mm to 2.5 mm. Variegation: Absent. Venation: Pattern: Parallel. Color of the midvein: Upper surface: RHS 147A. Lower surface: RHS 146A with a touch of purple (RHS N77A).

Peduncle:

*Quantity per plant*.—1 to 2.

*Number of flowers per peduncle*.—10 to 15.

*Length*.—55.0 cm to 60.0 cm.

*Diameter*.—4.9 mm to 5.4 mm.

*Strength*.—Strong.

*Aspect*.—Upright to slightly pendant.

*Texture*.—Smooth.

*Color*.—Mix of brown (RHS 200B) and yellow-green (RHS 146C).

*Internode length*.—4.0 cm to 5.0 cm.

Inflorescence description:

*Appearance*.—Upright to slightly pendant, panicle inflorescence with bilaterally symmetrical flowers that open in succession beginning with the lowermost flower.

*Number of inflorescences*.—1 to 2.

*Inflorescence size*.—Height (from base to tip): 250.0 mm to 280.0 mm.

*Flowering time*.—First flowers can be expected 10 to 11 months after planting in a 12-cm pot.

*Flower*.—Height: 68.0 mm to 73.0 mm. Diameter: 77.0 mm to 82.0 mm. Depth of lip: 18.0 mm to 20.0 mm.

*Flower longevity*.—On the plant: 14 to 18 weeks.

*Flower shape*.—Convex.

*Fragrance*.—Absent.

*Flower bud*.—Average size: Medium to large. Length: 21.0 mm to 23.0 mm. Width: 17.0 mm to 19.0 mm. Shape: Egg shaped. Color: Yellow-green (RHS 144C) with diluting dark purplish-red flecks (RHS N79A).

*Petals*.—Arrangement: Open/free. Shape: Semi-circular. Apex: Rounded asymmetric. Margin: Moderately undulated. Length (from base to tip): 36.0 mm to 38.0 mm. Width: 41.0 mm to 43.0 mm. Position of the broadest part of the petal: Toward the base. Color (when fully opened): Upper surface: Basic color: Light yellow-green (between RHS 145C and 150D). Over color: Absent. Lower surface: Basic color: Light yellow-green (RHS 145C). Over color: Diluting flecks (between RHS N79C and N77B). Number of spots and stripes on the petals (upper surface): Flecks: medium. Color of spots and stripes on the petals (upper surface): Flecks are darker in the centrum (RHS 187B) and become lighter toward the margin (RHS N79C). Density of netting of the petals (upper surface): None. Color of the netting (upper surface): None.

*Dorsal sepal*.—Shape: Elliptic. Apex: Obtuse symmetric. Margin: Entire. Length (from base to tip): 46.0 mm to 48.0 mm. Width: 31.0 mm to 33.0 mm. Position of the broadest part of the dorsal sepals: In the middle. Color (when fully opened): Upper surface: Basic color: Light yellow-green (RHS 145C). Over color: Absent. Lower surface: Basic color: Light yellow-green (RHS 145C). Over color: Yellow-green (RHS 145A) and diluting dark purplish-red flecks (RHS N79B). Number of spots and stripes on the dorsal sepals (upper surface): Medium flecks on the base. Color of spots and stripes on the dorsal sepals (upper surface): Flecks are darker in the centrum (RHS 187B) and become lighter toward the margin (RHS N79C). Density of netting of the dorsal sepals (upper surface): None. Color of the netting (upper surface): None.

*Lateral sepals*.—Shape: Ovate. Apex: Obtuse symmetric. Margin: Entire. Length (from base to tip): 39.0 mm to 41.0 mm. Width: 28.0 mm to 30.0 mm. Position of the broadest part of the lateral sepals: At the base. Color (when fully opened): Upper surface: Basic color: Light yellow-green (RHS 145C). Over color: Absent. Lower surface: Basic color: Light yellow-green (RHS 145C). Over color: Diluting dark purplish-red flecks (RHS N79B) and yellow-green middle vein (RHS 145A). Number of spots and stripes on the lateral sepals (upper surface): Few flecks at the base. Color of spots and stripes on the lateral sepals (upper surface): Flecks are darker in the centrum (RHS 187B) and become lighter toward the margin (RHS N79C). Density of netting of the lateral sepals (upper surface): None. Color of the netting (upper surface): None.

*Labellum* (*lip*).—Whiskers: Present. Length of whiskers: 3.0 mm to 5.0 mm. Color of whiskers: Very light purple (RHS 75C) and yellow tips (RHS 9A). Pubescence on the lip: Absent.

*Lateral lobe*.—Shape: Type IV (as described in the International Union for the Protection of New Varieties of Plants (UPOV) Test Guidelines for *Phalaenopsis*); weakly spatulate. Margin: Entire. Length: 16.0 mm to 18.0 mm. Width: 8.0 mm to 10.0 mm. Color: Upper surface: Dark red (RHS 187A and 187B) at the base; greenish-yellow (RHS 6A) at the margin on one side and white (RHS NN155C) toward margin on the other side. Lower surface: Diluting dark red (RHS 187A) at the base; yellow (RHS 6A) at the margin on one side and white (RHS NN155C) toward margin on the other side. Number of spots and stripes on the lateral lobe: None. Color of spots and stripes on the lateral lobe: None. Density of netting of the lateral lobe: None. Color of the netting: None.

*Apical lobe*.—Shape: Rhombic. Margin: Entire. Length: 22.0 mm to 24.0 mm. Width: 21.0 mm to 23.0 mm. Color: Upper surface: Greenish-yellow (RHS 2B) at the base; red (RHS 181A) and yellowish-pink (RHS 181D) toward the whiskers. Lower surface: White (RHS NN155C) in the middle; greenish-yellow (RHS 2B) and red wings (RHS 182B). Number of spots and stripes on the apical lobe: None. Color of spots and stripes on the apical lobe: None. Density of netting of the apical lobe: None. Color of the netting: None.

*Callus*.—Average size: Small. Height: 4.0 mm to 5.0 mm. Length: 3.0 mm to 4.0 mm. Width: 3.0 mm to 4.0 mm. Color: Dark red (RHS 187A) and light yellow (RHS 5A) at the base of two sides.

Reproductive organs:

*Column*.—Length: 9.0 mm to 11.0 mm. Diameter: 5.0 mm to 6.0 mm. Color: White (RHS NN155C).

*Pollinia*.—Quantity: 2. Diameter: 0.8 mm to 1.0 mm. Color: Orange-yellow (RHS 23A).

*Ovary*.—Length: 12.0 mm to 14.0 mm. Diameter: 2.0 mm to 3.0 mm.

*Pedicel*.—Length: 39.0 mm to 41.0 mm. Diameter: 3.0 mm to 4.0 mm. Texture: Smooth. Color: Light yellow-green (RHS 145B), flecked at the base (RHS N77A and N77B) and light yellow-green (RHS 145C) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALGOPXO' differs from female parent plant '21864-014' (unpatented) in that 'PHALGOPXO' has very light purple whiskers with yellow tips and flowers with a flecked pattern, whereas '21864-014' white whiskers and flowers with a spotted pattern.

'PHALGOPXO' differs from male parent plant '01-2083' (unpatented) in that 'PHALGOPXO' has flowers with a main color of light yellow-green and very light purple whiskers with yellow tips, whereas '01-2083' has flowers with a main color of dark red and purple-red whiskers. Additionally, 'PHALGOPXO' has smaller flowers than '01-2083'.

'PHALGOPXO' is most similar to the commercial *Phalaenopsis* plants named 'PHALFUXE' (U.S. Plant Pat. No. 29,450) and 'PHALDRYLO' (unpatented). 'PHALGOPXO' differs from the commercial variety 'PHALFUXE' in that 'PHALGOPXO' has rounded petal apexes and obtuse dorsal sepal apexes, whereas 'PHALFUXE' has emarginated petal apexes and rounded dorsal sepal apexes. Additionally, 'PHALGOPXO' has shorter lateral sepals and narrower dorsal sepals than 'PHALFUXE'.

'PHALGOPXO' differs from the commercial variety 'PHALDRYLO' in that 'PHALGOPXO' has rounded petal apexes and obtuse dorsal sepal apexes, whereas 'PHALDRYLO' has obtuse petal apexes and emarginated dorsal sepal apexes. Additionally, 'PHALGOPXO' has shorter lateral sepals than 'PHALDRYLO'.

I claim:

1. A new and distinct variety of *Phalaenopsis* plant named 'PHALGOPXO', substantially as described and illustrated herein.

* * * * *